United States Patent [19]

Anderson et al.

[11] Patent Number: 5,265,602
[45] Date of Patent: Nov. 30, 1993

[54] RING-TO-RING CARDIAC ELECTROGRAM PACEMAKER

[75] Inventors: Russell E. Anderson, Marine on St. Croix; James D. Reinke, Maple Grove; Kirk S. Vadnais, Roseville; Terrence R. Hudrlik, Fridley, all of Minn.

[73] Assignee: Medtronic, Inc., Minneapolis, Minn.

[21] Appl. No.: 912,455

[22] Filed: Jul. 13, 1992

[51] Int. Cl.⁵ .................................. A61N 1/368
[52] U.S. Cl. .............................. 607/9; 128/786; 128/419 P
[58] Field of Search ............. 128/419 PG, 419 P, 783, 128/786, 901, 696

[56] References Cited

U.S. PATENT DOCUMENTS

| | | | |
|---|---|---|---|
| 4,387,717 | 6/1983 | Brownlee et al. | 128/419 |
| 4,556,063 | 12/1985 | Thompson et al. | 128/419 |
| 4,579,119 | 4/1986 | Callaghan | 128/419 |
| 4,585,004 | 4/1986 | Brownlee | 128/419 |
| 4,913,146 | 4/1990 | DeCote, Jr. | 128/419 PG |
| 4,955,376 | 9/1990 | Callaghan et al. | 128/419 PG |
| 5,154,171 | 10/1992 | Chirife | 128/419 PG |

*Primary Examiner*—William E. Kamm
*Assistant Examiner*—George Manuel
*Attorney, Agent, or Firm*—Harold R. Patton; Gregory P. Gadson

[57] ABSTRACT

A pacemaker having two bipolar leads, one atrial, one ventricular, each with TIP and RING electrodes, configured as for conventional bipolar pacing/sensing in both chambers. Switching circuitry in the pacemaker is operable to select from among various possible sensing configurations, including one configuration in which sensing is performed between the ring electrodes of the respective pacing/sensing leads. Pacing is preferably performed in a conventional unipolar configuration in each chamber, from the respective tip electrodes. The "ring-to-ring" EGM signal is applied to filtering and EGM amplifier circuitry, and then provided to a telemetry system for transmission to an external receiver. The ring-to-ring EGM signal possesses the high resolution properties of conventional intracardiac signals, and is relatively unaffected by the after-potentials and tissue polarization effects that arise when the same lead is used for pacing and sensing. Additionally, the ring-to-ring EGM signal is a composite of atrial and ventricular electrical signals, and thus has an appearance similar to that of surface ECGs.

5 Claims, 7 Drawing Sheets

RING-TO-RING CARDIAC ELECTROGRAM PACEMAKER

FIELD OF THE INVENTION

This invention relates to the field of cardiac pacemakers, and more specifically to a method and apparatus for sensing electrical cardiac signals.

BACKGROUND OF THE INVENTION

Implantable cardiac pacemakers of varying degrees of sophistication and operational capability are well known in the art. Earlier pacemakers were simple by today's standards, typically being capable of pacing only in a single chamber of the patient's heart, and only at an asynchronous, fixed, and uninhibited pacing rate. Today, pacemakers are available which are capable of synchronous, inhibited pacing in both chambers, at a pacing rate which may be varied according to detected intrinsic cardiac activity or some other physiological indication of the patient's metabolic needs.

Pacemakers are most commonly operated in conjunction with one or more leads, for conveying cardiac stimulating pulses from the pacemaker to the patient's heart, and for conveying electrical cardiac signals from the heart to the pacemaker's sensing circuitry. At least two different types of pacemaker leads, unipolar and bipolar, are commonly known and used.

Unipolar leads have only a single electrode and a single electrical conductor therein. The electrode is disposed at or near the distal end of the lead, which is situated in some particular location in the patient's heart, for example at the apex of the heart in the right ventricle, in the atrial chamber, or in the coronary sinus. The single electrode and conductor of a unipolar lead are used both for sensing (that is, for conducting electrical cardiac signals from the heart to the pacemaker) and for pacing (that is, for delivering stimulating pulses from the pacemaker to the heart.

Bipolar leads have two electrodes and two electrically isolated conductors therein. Often, one electrode, called the "tip" electrode, is a conductive contact disposed at the distal end of the lead, while a second electrode, called the "ring" electrode, is a conductive ring disposed on the lead body some distance back from the distal end of the lead. One of the isolated conductors conducts signals between the pacemaker and the tip electrode, while the other conducts signals between the pacemaker and the ring electrode.

In the case of unipolar pacing and sensing, the electrically conductive pacemaker canister can serve as an indifferent electrode, with pacing and sensing occurring between the lead electrode and the pacemaker canister. In bipolar pacing and sensing, it is not necessary to use the pacemaker canister as an electrode in the pacing or sensing circuit, since pacing and sensing can occur between the tip electrode and the ring electrode, rather than between the tip electrode and the pacemaker canister as in a unipolar configuration.

As pacemaker functionality has become increasingly sophisticated and complex, it has become ever more important for the physician to monitor and obtain information about the pacemaker's operation. Accordingly, many pacemakers today are capable of transmitting, for example via radio-frequency telemetry, information about the pacemaker's current programmable parameter settings and the pacemaker's operational status. In addition, the telemetry system may be capable of transmitting a representation of the intracardiac electrogram. The electrical cardiac signal received on the pacemaker lead and provided to the pacemaker'sensing circuitry can also be applied to the telemetry system, and transmitted in either analog or digital form to an external receiver, where the intracardiac electrogram can be viewed on a strip chart or ECG monitor.

In order to verify or optimize operation of an implanted pacemaker, a physician must be able to determine, among other things, when a stimulating pulse has been delivered to a chamber of the heart, and whether the stimulating pulse possessed sufficient energy to elicit a response from that chamber of the heart (i.e., whether "capture" has been achieved). Such determinations can be difficult to make, particularly with some of the more advanced dual chamber, rate- or activity-responsive pacemakers in which the pacing rate may vary from one cardiac cycle to the next, and in which stimulating pulses may or may not be delivered depending upon sensed intrinsic cardiac activity.

Often, a physician will use a conventional surface electrocardiogram (surface ECG) equipment to monitor cardiac and pacemaker functions. Obtaining a surface ECG can involve placement of a dozen or more skin electrodes, and can be uncomfortable and inconvenient for the patient. In addition, cardiac signals are subject to attenuation and distortion when they pass through the patient's tissue to be received by surface electrodes, and this can complicate the interpretation of the signals and assessment of cardiac and pacemaker function. In some cases, the morphological aspects of an electrical cardiac signal that must be detected to accurately assess cardiac or pacemaker function are simply not revealed in the surface ECG. For example, in determining whether a pacemaker has achieved capture, the physician can look for an often subtle characteristic of the cardiac electrical signal known as an evoked response. Often, evoked responses to a stimulating pulse are not revealed in surface ECG tracings.

Intracardiac electrogram (EGM) signals, derived from the electrical cardiac signal on the pacemaker lead(s) and transmitted to an external programmer as described above, are also known to be useful in monitoring and verifying pacemaker operation. One perceived drawback to such intracardiac EGM signals, however, is that since the same lead is used for pacing and sensing, the high stimulating pulse voltage spike, after-potentials, and electrode-tissue polarizations render the intracardiac EGM system "blind" to the cardiac signal for a period of time immediately following the delivery of each stimulating pulse. Unfortunately, it is during this time period immediately following a stimulating pulse that is of most interest in determining whether capture has been achieved (i.e., whether there has been an evoked response).

Typically, in dual chamber pacing, atrial and ventricular EGM signals are detected using the same lead configuration (i.e., unipolar or bipolar) as used for pacing in the respective chambers. For example, if atrial bipolar pacing between the tip and ring electrodes on the atrial lead, the atrial tip and ring electrodes will also provide the inputs to the atrial sense amplifier.

With conventional surface ECG electrodes, the electrogram signal viewed by the physician on the ECG monitor or strip chart represents a composite of the atrial and ventricular signals of the heart. In the inventors' experience, it has generally been found that physicians are generally more familiar with this type of ECG waveform than the separate atrial and ventricular signals provided from intracardiac electrodes. Since a surface ECG signal represents both the atrial and ventricular signals simultaneously, the physician can easily perceive the timing relationships between activity in the two chambers, and the relative magnitudes of atrial and ventricular signals. With the separate atrial and ventricular signals provided from intracardiac electrodes, on the other hand, the physician must somehow view both signals at once, such as on a dual-trace ECG monitor or a dual-trace strip chart recorder, in order to ascertain information about the interaction or coordination of atrial and ventricular cardiac activity, and about the operation of the pacemaker.

Thus, although intracardiac electrogram signals offer greater resolution (i.e., less distortion and attenuation of cardiac signals) than surface ECG signals, intracardiac pacing leads are not effective for all purposes, since the above-noted problems of after-potentials and electrode-tissue polarizations render the pacing lead "blind" to electrical cardiac activity immediately following delivery of a stimulating pulse from that lead.

One solution for resolving the trade-off between surface ECG and intracardiac EGM signals was proposed by Brownlee et al. in U.S. Pat. No. 4,387,717. In the '717 patent, Brownlee et al. appear to suggest the use of a separate, large surface area electrode, separate from any pacing electrode, to perform sensing. According to the '717 patent, the large surface area sensing electrode, in conjunction with the pacemaker canister as an indifferent electrode, can provide both atrial and ventricular signals to the pacemaker's EGM amplifier. However, it is noted in the '717 patent that the large surface area electrode must be situated far enough away from the pacing electrode so as to avoid the above-noted problems with after-potentials and tissue polarization.

Another solution that has been proposed in the prior art is described in U.S. Pat. No. 4,585,004 to Brownlee. In the '004 patent, Brownlee apparently suggests the use of a separate "data lead", in addition to the pacing lead, for conveying intracardiac signals to the pacemaker's EGM amplifier. According to the '004 patent, the data lead is provided with two ring electrodes which are electrically coupled to a common lead conductor. It is believed by the inventor's that the need for a separate data lead for EGM sensing is undesirable, especially if the two leads used for dual-chamber pacing must also be implanted.

SUMMARY OF THE INVENTION

In view of the foregoing considerations relevant to pacemaker pacing and sensing and the desirability of monitoring cardiac electrical activity and pacemaker operation, it is believed by the inventors that there has yet to be shown in the art a pacing and sensing arrangement that fully addresses the various perceived shortcomings of known techniques.

It is accordingly a feature of the present invention that a pacemaker is provided in which offers the desirable properties of both ECG and EGM sensing.

In particular, it is a feature of the present invention that a composite atrial and ventricular EGM signal is provided by a pacemaker for transmission via the pacemaker's telemetry channel.

It is another feature of the present invention that the composite signal is of sufficient resolution to reveal information about evoked cardiac responses to pacing stimuli.

Another feature of the present invention is that the sensing configuration is such that problems with after-potentials and electrode/tissue polarization are avoided.

It is yet another feature of the present invention that a separate lead dedicated to the intracardiac electrogram sensing function is not required.

In accordance with the present invention a pacemaker having two bipolar leads (i.e., one atrial, one ventricular, each with TIP and RING electrodes) is implanted in a patient. The leads are configured as for conventional bipolar pacing/sensing in both chambers. Switching circuitry in the pacemaker is operable to select from among various possible lead configurations, including one configuration in which intracardiac electrogram (EGM) sensing is performed between the ring electrodes of the respective pacing/sensing leads. Pacing is preferably performed in a conventional unipolar configuration in each chamber, from the respective tip electrodes. The "ring-to-ring" EGM signal is applied to filtering and EGM amplifier circuitry, and then provided to a telemetry system for transmission to an external receiver. The ring-to-ring EGM signal possesses the high resolution properties of conventional intracardiac signals, and is relatively unaffected by the after-potentials and tissue polarization effects that arise when the same lead is used for pacing and sensing. Additionally, the ring-to-ring EGM signal is a composite of atrial and ventricular electrical signals, and thus has an appearance similar to that of surface ECGs.

BRIEF DESCRIPTION OF THE DRAWINGS

The foregoing and other aspects of the present invention will be best understood with reference to the following detailed description of a specific embodiment of the invention, when read in conjunction with the accompanying drawings, wherein.

DETAILED DESCRIPTION OF A SPECIFIC EMBODIMENT OF THE INVENTION

Figure 1:
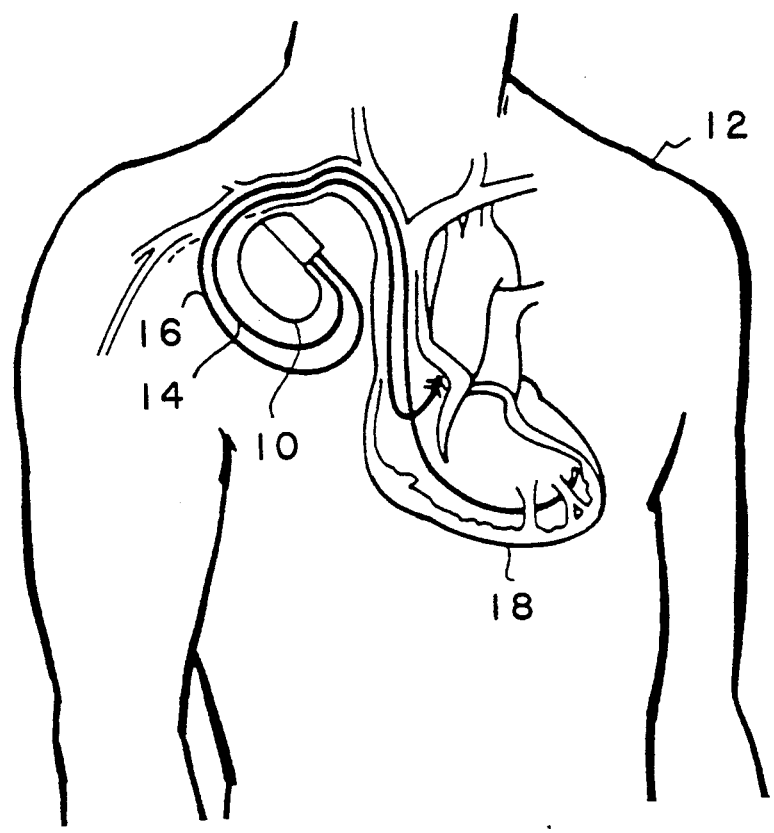
FIG. 1 is an illustration of a pacemaker and pacemaker leads in accordance with one embodiment of the present invention, implanted in a patient.

In FIG. 1, a pacemaker 10 in accordance with one embodiment of the present invention is shown implanted in a patient 12. Transvenous atrial and ventricular leads 14 and 16, respectively, conduct signals between the heart 18 and pacemaker 10, in a conventional manner.

Figure 2:
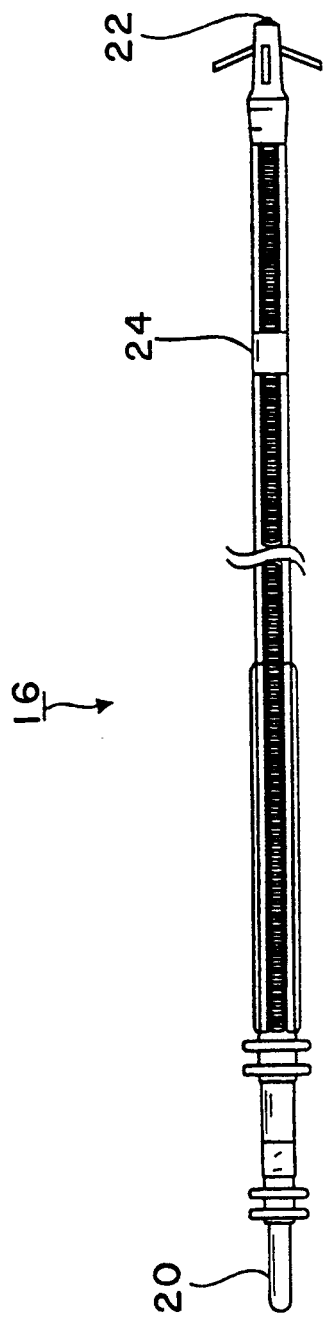
FIG. 2 is an enlarged view of a pacemaker lead from FIG. 1.

FIG. 2 is a somewhat enlarged view of bipolar ventricular lead 16 from FIG. 1. On its proximal end, lead 16 has a connector pin 20 adapted to be received in a connector block on pacemaker 10, in a manner well known in the prior art. A "tip" electrode 22 is disposed on the extreme distal end of lead 16, and at least one "ring" electrode 24 is disposed some distance back from the distal end along the body of lead 16. Bipolar atrial lead 14 is substantially the same as lead 16, except that atrial lead 14 is commonly provided with a "J" shape at its distal end to facilitate the disposition of the lead 14 within the atrium of the heart. A great many bipolar implantable pacing/sensing electrodes have been shown in the prior art that are suitable for the purposes of the present invention, and it is believed by the inventors that selection and use of a particular type of bipolar lead is not critical to the present invention. One lead suitable for the purposes of the present invention is the Model 4012 lead manufactured by and commercially available from Medtronic, Inc., Minneapolis, Minn.

For the purposes of the present description of a particular embodiment of the invention, the cardiac signals received by leads 14 and 16 shall be referred to as follows: the signal received at the tip electrode of ventricular lead 16 will be designated VTIP, and the signal at the ring electrode of ventricular lead 16 will be designated VRING; similarly, ATIP and ARING will be used to designate the signals received at the tip and ring electrodes, respectively, of atrial lead 14. To the extent that the pacemaker canister is included in the pacing/sensing arrangement as a common or indifferent electrode, the electrical signal associated with the pacemaker canister will be designated CASE.

Figure 3:
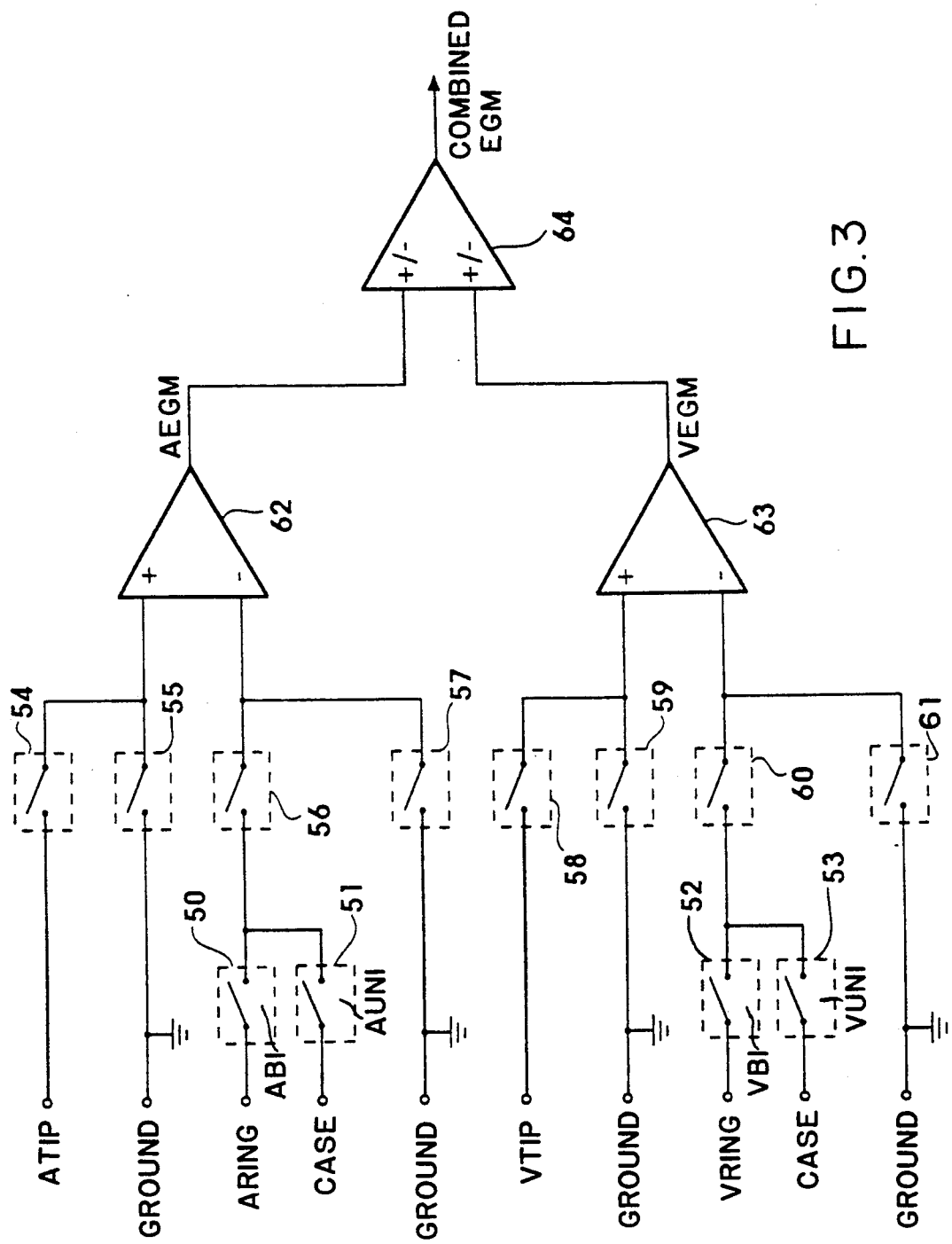
FIG. 3 is a schematic diagram of a portion of the circuitry in the pacemaker of FIG. 1.

Turning now to FIG. 3, EGM circuitry from the pacemaker 10 of FIG. 1 is shown in schematic form. It is to be understood that the present invention may be practiced in the context of many different pacemakers presently known and commercially available, such as the Medtronic Elite ™ . Pacemaker 10 should include a telemetry system capable of transmitting an analog EGM signal to an external receiver; such a telemetry system is disclosed, for example, in U.S. Pat. No. 4,556,063 issued to Thompson et al. on Dec. 3, 1985 and entitled "Telemetry System for a Medical Device", which patent is hereby incorporated by reference in its entirety.

As shown in FIG. 3, the circuitry therein is coupled to the ATIP, ARING, VTIP, VRING, and CASE signals previously described with reference to FIGS. 1 and 2; the circuit is also coupled to ground at several points, as shown in the Figure. The circuitry of FIG. 3 includes a plurality of switches 50 through 61. It is to be understood, of course, that switches 50 through 61 may be implemented in a number of ways, although in the presently preferred embodiment, these switches are implemented as simple transistors in an integrated circuit, as will be hereinafter shown in greater detail with reference to FIG. 7. In addition, it is contemplated that switches 50 through 61 will not be physically actuated, but instead will be actuated under control of software or hardware in the control circuitry of pacemaker 10. For the purposes of the following description, each one of the switches 50 through 61 will be described as being "open" when it is in the position shown in FIG. 3, while a switch which establishes a connection between its terminals will be described as "closed".

The circuit of FIG. 3 further includes an atrial EGM amplifier 62, a ventricular EGM amplifier 63, and a combined EGM amplifier 64. EGM amplifiers are well-known in the pacemaker field, and it is believed by the inventors that the present invention may be practice in conjunction with many different types of EGM amplifiers, such as that disclosed in the above-reference Thompson '063 patent. The output of combined EGM amplifier 64 is available to be applied to the pacemaker's telemetry system for transmission to an external receiver. As previously noted, the telemetry system may be of the type described in the above-referenced Thompson et al. patent.

Switches 50 and 51 in FIG. 3 are provided to allow selection of either atrial unipolar or atrial bipolar sensing in pacemaker 10. Similarly, switches 52 and 53 are provided to allow selection of either ventricular unipolar or ventricular bipolar sensing in pacemaker 10. As previously noted, controlling the status of switches 50 through 53 is preferably accomplished under control of the hardware or software associated with the pacing control circuitry of pacemaker 10; thus, for example, a command issued from an external programmer indicating that atrial bipolar sensing is to be performed would cause the pacemaker's control circuitry to activate certain of the transistor(s) comprising switches 50 and 51, so that switch 50 is closed and switch 51 is open. Switches 50 and 51 and switches 52 and 53 may be independently controlled, so that, for example, atrial unipolar and ventricular bipolar sensing may be selected.

With the arrangement of switches 50 through 61 shown in FIG. 3, there are a number of possible combinations of sensing signals which can be made. These combinations are summarized in the following Table 1:

TABLE 1

| AEGM | SWITCHES | | | | VEGM | SWITCHES | | | | COMBINED EGM |
|---|---|---|---|---|---|---|---|---|---|---|
| | 54 | 55 | 56 | 57 | | 58 | 59 | 60 | 61 | |
| ATIP TO GROUND | Closed | Open | Open | Closed | VTIP TO GROUND | Closed | Open | Open | Closed | ATIP-VTIP |
| ARING TO GROUND | Open | Closed | Closed | Open | VRING TO GROUND | Open | Closed | Closed | Open | ARING-VRING |
| ATIP TO ARING/CASE | Closed | Open | Closed | Open | VTIP TO VRING/CASE | Closed | Open | Closed | Open | SUMMED |
| ATIP TO ARING/CASE | Closed | Open | Closed | Open | GROUND TO GROUND | Open | Closed | Open | Closed | AEGM |
| GROUND TO GROUND | Open | Closed | Open | Closed | VTIP TO VRING/CASE | Closed | Open | Closed | Open | VEGM |
| ARING/CASE TO GROUND | Open | Closed | Closed | Open | GROUND TO GROUND | Open | Closed | Open | Closed | ARING |

As will be hereinafter described, it is the configuration of switches 50 through 61 which results in an ARING-VRING signal, or an ATIP-VTIP signal, being produced at the COMBINED EGM output of the circuitry of FIG. 3 that is of particular relevance to the presently disclosed embodiment of the invention.

Figure 4:
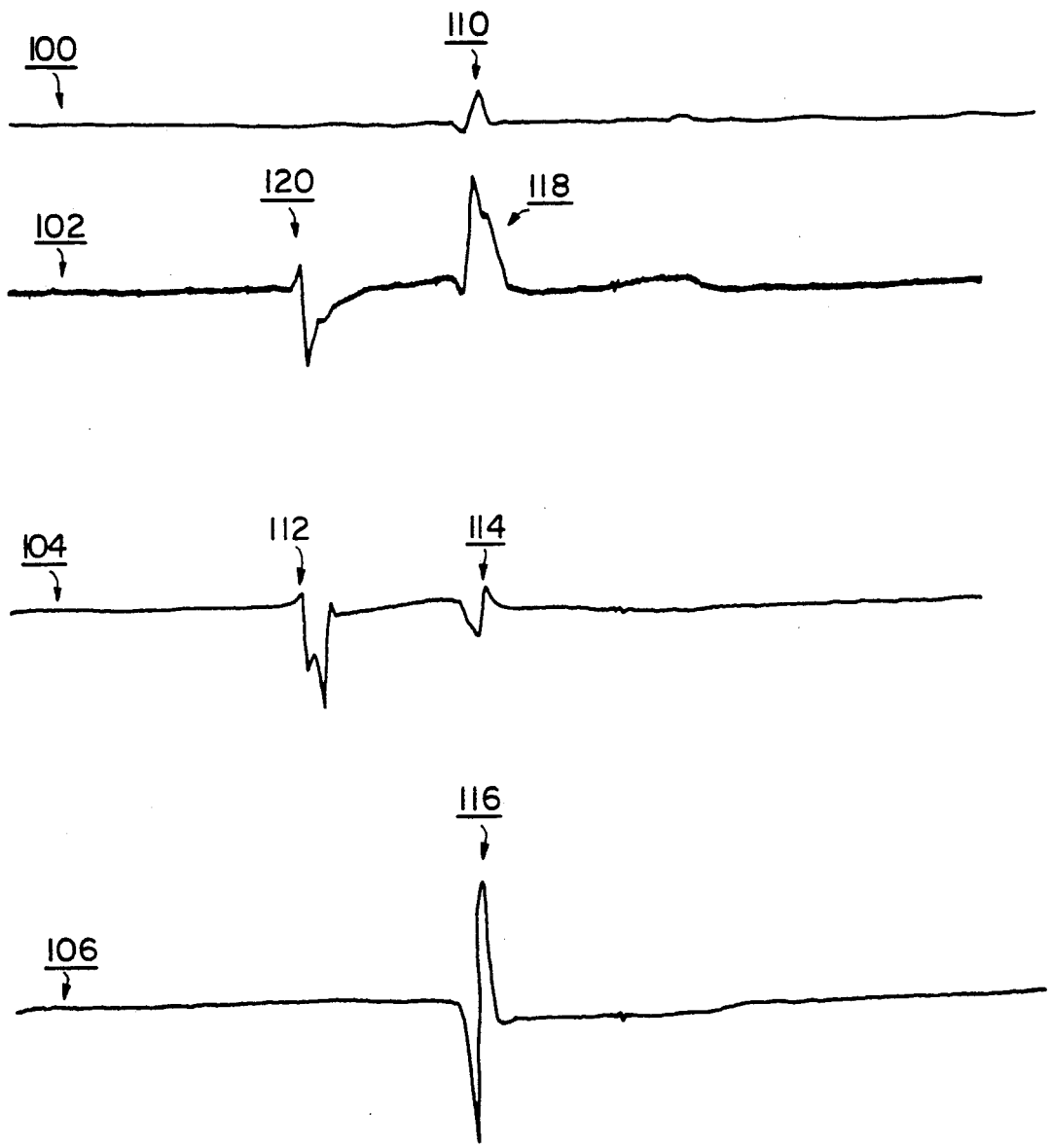
FIG. 4 is a set of electrical cardiac signal waveforms conducted on the pacemaker leads from FIGS. 1 and 2.

Turning now to FIG. 4, a graph of various cardiac waveforms is shown. In FIG. 4 and later Figures, it is to be understood that the several waveform traces in each Figure are time-synchronized, such that a given horizontal position in the Figures corresponds to the same time in each of the waveforms depicted.

In FIG. 4, a first waveform 100 corresponds to the surface ECG signal taken from a patient using conventional surface electrodes. Waveform 100 is what most physicians are accustomed to seeing and analyzing. A QRS complex designated generally as 110 in FIG. 4 is the most pronounced feature of the surface ECG signal, and the P-wave and T-wave phases of the cardiac signal are barely discernable, if at all.

Waveform 104 in FIG. 4 corresponds to the ATIP-ARING sensing configuration commonly available with prior art pacemakers; this signal corresponds to the voltage between the atrial tip and ring electrodes. The more prominent feature of waveform 104 is the atrial (P-wave) phase of the cardiac cycle, designated generally as 112 in FIG. 4. A so-called "far-field R-wave" (FFR) 114 is also visible in waveform 104, this corresponding to the detection of ventricular activity in the atrial channel. Far-field R-waves are visible in the atrial channel because ventricular signals typically are of a much greater magnitude than atrial signals, and conduction of these relatively signals through the heart tissue and blood from the ventricle to the atrium allows the QRS complex to be detected by an atrial lead. Atrial signals, being of relatively smaller magnitude, are typically not detected by a ventricular lead; thus, there is typically no "far-field P-wave" visible in the ventricular channel.

Waveform 106 in FIG. 4 corresponds to the voltage between the ventricular tip and ring electrodes (VTIP to VRING sensing). The ventricular signal (QRS-complex) is designated 116 in waveform 106, and as previously noted, little if any atrial activity is received by the ventricular lead.

Waveform 102 in FIG. 4 corresponds to the VRING to ARING sensing configuration in accordance with the presently disclosed embodiment of the invention. Note in waveform 102 that both a well-defined ventricular QRS-complex 118 and a well-defined atrial P-wave 120 are visible, thus enabling a physician to derive more information from waveform 102 than from either waveform 100, waveform 104, or waveform 106.

Figure 5:
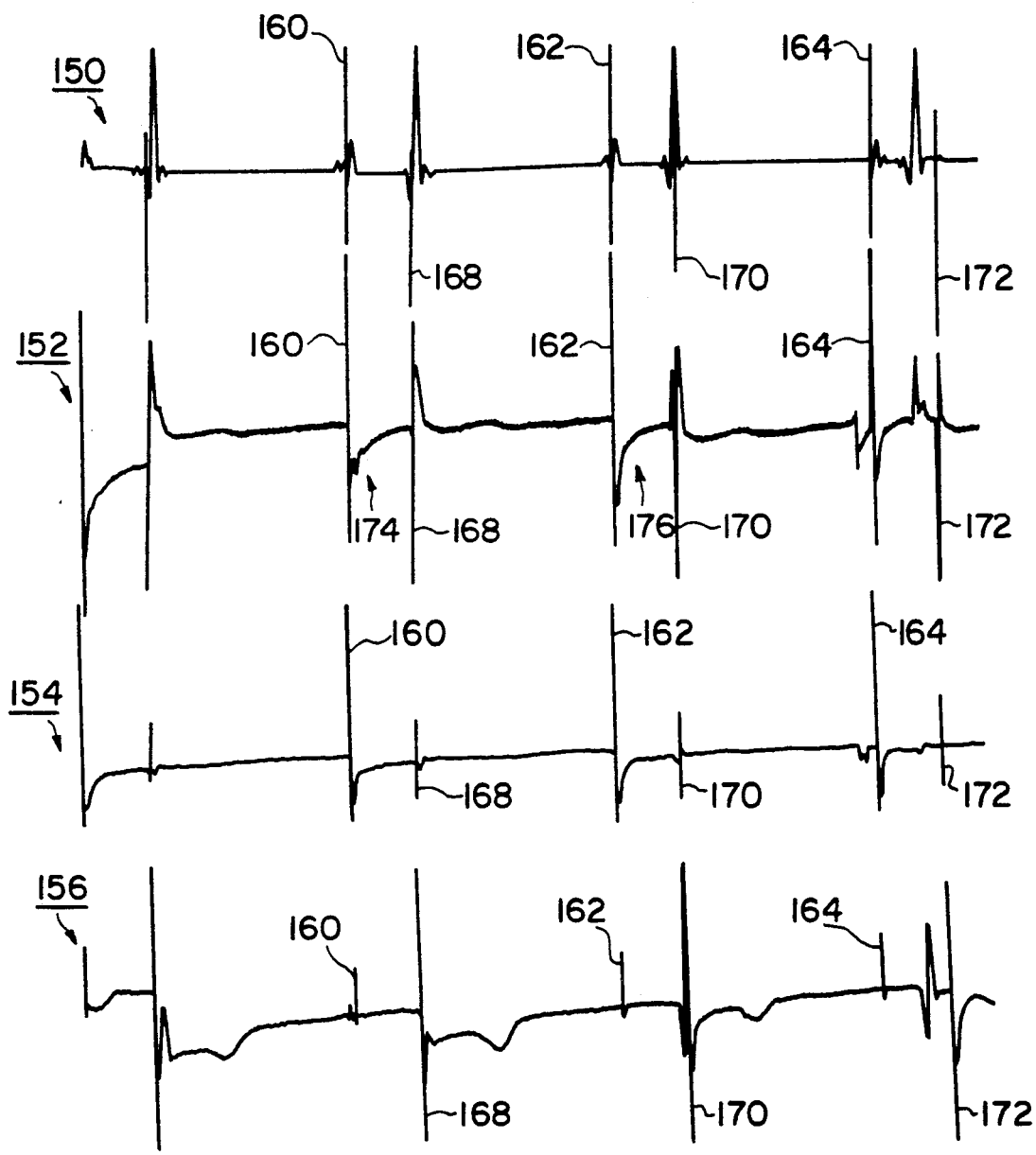
FIG. 5 is another set of electrical cardiac signal waveforms conducted on the pacemaker leads from FIGS. 1 and 2.

In FIG. 5, another set of cardiac waveforms is shown. Waveform 150 corresponds to a surface ECG signal from the patient. Waveform 154 is an ATIP-ARING (atrial bipolar sensing) signal, waveform 156 is a VTIP-VRING (ventricular bipolar sensing) signal, and waveform 152 is an ARING-VRING signal. In the sequence of cardiac cycles depicted in the waveforms of FIG. 5, pacemaker is delivering atrial and ventricular pacing pulses at an asynchronous, uninhibited rate with a programmed A-V delay of 150-mSec. In each of the waveforms 150, 152, 154, and 156, the atrial pacing pulses are designated as 160, 162, and 164. Ventricular pacing pulses are designated as 168, 170 and 172. In the ATIP-ARING waveform 154, provided from the atrial TIP and RING electrodes, atrial pacing pulses 160, 162, and 164 appear to have a greater magnitude than ventricular pacing pulses 168, 170, and 172, since the atrial lead is in much closer proximity to the atrium than the ventricular lead is. Little or no information about ventricular activity is discernible from waveform 154. In VTIP-VRING waveform 156, atrial pacing pulses 160, 162, and 164 appear to have a much lower magnitude than ventricular pacing pulses 168, 170, and 172, the ventricular lead being in closer proximity to the ventricle than the atrial lead. Little or no information about atrial activity is discernible from waveform 156.

In the surface electrode waveform 150 in FIG. 5, both atrial and ventricular pacing pulses are visible. However, as would be apparent to one of ordinary skill in the art of cardiac signals, little can be determined about evoked cardiac responses to stimulating pulses in surface electrode waveform 150. On the other hand, from ARING-VRING waveform 152, an evoked atrial response 174 to atrial stimulating pulse 160 is discernible, whereas it is not in either of waveforms 150, 154, or 156. Moreover, the lack of an evoked atrial response at 176 to atrial stimulating pulse 162 can also be seen in waveform 154, whereas the presence or absence of an evoked response to stimulating pulse 162 cannot be determined in the other waveforms.

Figure 6:
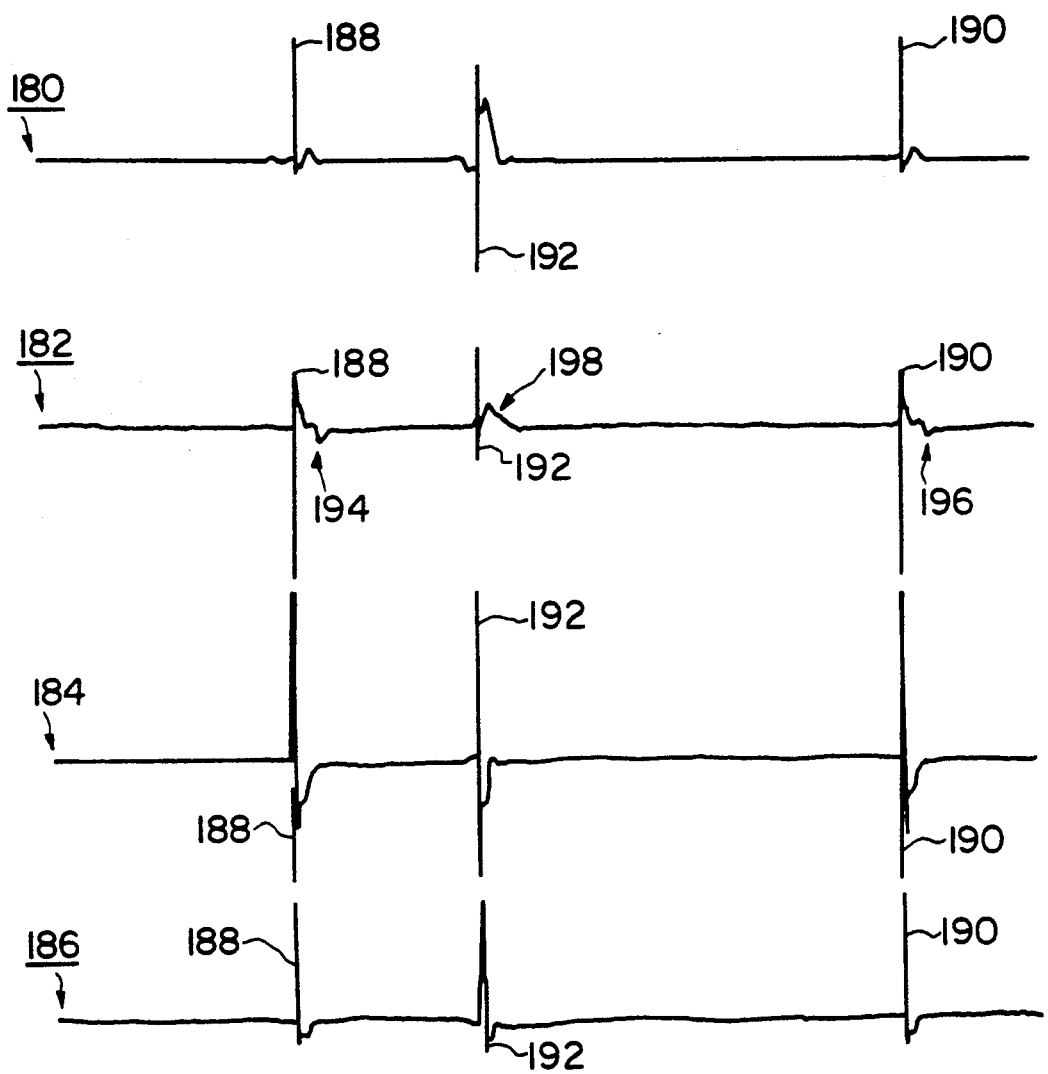
FIG. 6 is another set of electrical cardiac signal waveforms conducted on the pacemaker leads from FIGS. 1 and 2.

Turning now to FIG. 6, still another set of EGM waveforms is shown, where waveform 180 is a surface ECG signal, waveform 184 is an ATIP-CASE (unipolar atrial sensing) signal, waveform 186 is a VTIP-CASE (unipolar ventricular sensing) signal, and waveform 182 is an ARING-VRING signal. In FIG. 6, atrial pacing pulses 188 and 19? are shown, and ventricular pacing pulse 192 is shown. In the unipolar sensing waveforms 184 (atrial unipolar) and 186 (ventricular unipolar), evoked responses to stimulating pulses 188, 190, and 192 cannot be discerned. However, in ARING-VRING waveform 182, an evoked atrial response 194 to atrial stimulating pulse 188 is visible, an evoked atrial response 196 to atrial stimulating pulse 190 is visible, and an evoked ventricular response 198 to ventricular stimulating pulse 192 is visible.

Figure 7:
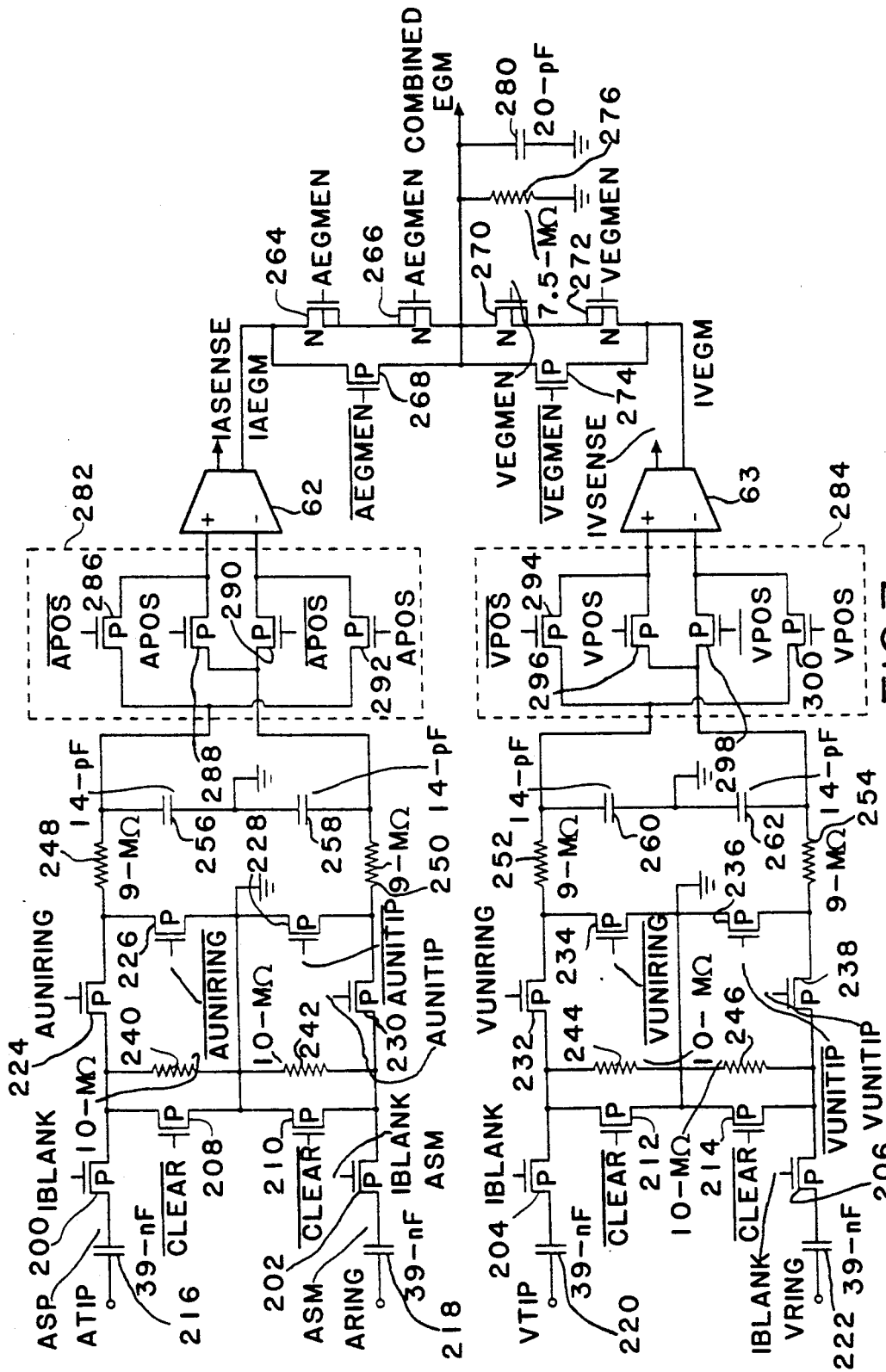
FIG. 7 is a schematic diagram of a specific embodiment of switching circuitry from FIG. 3.

Referring to FIG. 7, a schematic diagram of a specific implementation of a portion of the circuitry of FIG. 3 is shown. The circuitry of FIG. 7 is preferably implemented as part of an integrated circuit, but may also be implemented using discrete components.

In FIG. 7, transistors 200, 202, 204, and 206 are gated by a signal IBLANK to disconnect the EGM circuitry including EGM amplifiers 62 and 63 from the TIP and RING electrodes during delivery of pacing pulses and during the fast recharge cycle of the pacing output capacitors. This prevents amplifiers 62 and 63 from saturating.

Transistors 208, 210, 212, and 214 in FIG. 7 are gated by a signal $\overline{\text{CLEAR}}$ which is asserted (negative) along with IBLANK to hold the inputs to amplifier 62 and 63 at ground when TIP and RING are disconnected therefrom. Transistors 208, 210, 212, and 214 remain conductive slightly longer than transistors 200, 202, 204, and 206 (i.e., $\overline{\text{CLEAR}}$ is asserted slightly longer than IBLANK during pace and fast recharge) to allow 39-nF capacitors 216, 218, 220, and 222 to be cleared of any voltage which may have accumulated during pace and recharge.

Transistors 224 and 226 are gated by signals AUNIRING and $\overline{\text{AUNIRING}}$ (it being understood that $\overline{\text{AUNIRING}}$ is simply the logical negation of AUNIRING), respectively. Also, transistors 228 and 230 are gated by signals AUNITIP and $\overline{\text{AUNITIP}}$. Similarly, in the ventricular channel, transistors 232 and 234 are gated by signals VUNIRING and $\overline{\text{VUNIRING}}$, while transistors 236 and 238 are gated by signals VUNITIP and $\overline{\text{VUNITIP}}$. Transistors 224, 226, 228, 230, 232, 234, 236, and 238 perform the switching function previously described with reference to FIG. 3, allowing amplifiers 62 and 63 to receive tip-to-ring, tip-to-ground, or ringto-ground signals for their respective atrial or ventricular channels. When sensing either tip-to-ground or ring-to-ground, CASE is shorted to ground, forcing tip-to-ground, ring-to-ground to be equivalent to tip-to-case, ring-to-case. The output from transconductance amplifier 62, which has a gain factor of Gm, can thus be summarized as shown in the following Table 2 for the different possible combinations of AUNIRING and AUNITIP:

TABLE 2

| AUNIRING | AUNITIP | IAEGM |
|---|---|---|
| 0 | 0 | Gm x (TIP-RING) |
| 0 | 1 | Gm x (TIP-CASE) |
| 1 | 0 | Gm x (CASE-RING) |
| 1 | 1 | Gm x (CASE-CASE) |

Similarly, for ventricular EGM transconductance amplifier 63, the output for the different possible combinations of VUNIRING and VUNITIP is summarized in the following Table 3:

TABLE 3

| VUNIRING | VUNITIP | IVEGM |
|---|---|---|
| 0 | 0 | Gm x (TIP-RING) |
| 0 | 1 | Gm x (TIP-CASE) |
| 1 | 0 | Gm x (CASE-RING) |
| 1 | 1 | Gm x (CASE-CASE) |

10-MΩ resistors 240, 242, 244, and 246, along with capacitors 216, 218, 220, and 222, form a high-pass filter network with a corner frequency of about 0.4-Hz. 9-MΩ resistors 248, 250, 252, and 254 and 14-pF capacitors 256, 258, 260, and 262 form a low-pass filter to reject high frequencies such as the 175-kHz uplink-/downlink frequency. The low-pass corner frequency is at approximately 1.3-kHz in the preferred embodiment.

Differential transconductance amplifiers 62 and 63 convert the EGM differential voltages applied thereto into currents. The currents can then by easily summed for a combined atrial and ventricular EGM signal. As shown in FIG. 7, the output from atrial EGM amplifier 62 may be selectively applied to the COMBINED EGM output line by asserting an enabling signal AEGMEN that is applied to the gates of n-type transistors 264 and 266 (with the negated $\overline{\text{AEGMEN}}$ being applied to the gate of p-type transistor 268). Likewise, the output from ventricular EGM amplifier 63 may be selectively applied to the COMBINED EGM output line by asserting an enabling signal VEGMEN that is applied to the gates of n-type transistors 270 and 272 (with the negated $\overline{\text{VEGMEN}}$ being applied to the gate of p-type transistor 274). The outputs of amplifiers 62 and 63 may thus be summed by asserting both AEGMEN and VEGMEN. Of course, single channel (i.e., either atrial or ventricular) EGM signals can be provided on the COMBINED EGM output line by asserting only AEGMEN or VEGMEN.

7.5-MΩ resistor 276 and 20-pF capacitor 280 are used to turn the COMBINED EGM current signal back into a voltage, which can then be digitized and uplinked via the telemetry system. Resistor 276 and capacitor 280 are preferably selected to obtain the desired voltage range for the digitizing circuitry (not shown in the Figures), and to provide a low-pass filtering function with a corner frequency of 1-kHz. This low-pass filtering provides anti-aliasing protection for the digitizer.

In order that differenced AEGM and VEGM signals can be obtained in addition to summed AEGM and VEGM signals, switching circuits 282 and 284 have been provided. An APOS signal is applied to the gates of p-type transistors 286, 288, and 290. A VPOS signal is applied to the gates of p-type transistors 292, 294, 296, 298, and 300. As would be appreciated by those of ordinary skill in the circuit art, depending upon whether APOS or VPOS is asserted the TIP and RING signals in each channel can be reversed before they are applied to the inverting and non-inverting inputs of amplifiers 62 and 63. By inverting the sign of the output from amplifiers 62 or 63, a signal representing the difference, rather than the sum, of the atrial and ventricular sensing signals may be obtained on the COMBINED EGM output line.

From the foregoing detailed description of a particular embodiment of the present invention, it should be apparent that a method and apparatus for providing a composite atrial and ventricular EGM signal to a pacemaker's telemetry system is disclosed. Although a particular embodiment of the present invention has been described herein in detail, it is to be understood that such description has been provided for the purposes of illustration only, and is not intended to limit the scope of the present invention as defined in the appended claims. For example, while specific values for various circuit components shown in the Figures have been stated, these values may be different for different implementations of the present invention. It is believed by the inventors that various substitutions, alterations, and modifications may be made to the embodiment described herein without departing from the spirit and scope of the present invention as set forth in the claims.

What is claimed is:

1. An implantable cardiac pacemaker system, comprising:
   a pulse generator, adapted to produce cardiac stimulating pulses;
   a bipolar transvenous atrial pacing/sensing lead coupled to said pulse generator, said atrial lead having a first atrial conductor therein coupled to a tip electrode at a distal end of said lead and a second atrial conductor therein coupled to a ring electrode spaced apart from said tip electrode, said distal end of said lead disposed in a patient's atrium such that electrical signals in said atrium are received by said atrial ring electrode and conducted by said first atrial conductor;
   a bipolar transvenous ventricular pacing/sensing lead coupled to said pulse generator, said ventricular lead having a first ventricular conductor therein coupled to a tip electrode at a distal end of said lead and a second ventricular conductor therein coupled to a ring electrode spaced apart form said tip electrode, said distal end of said ventricular lead being disposed in the patient's ventricle such that electrical signals in said ventricle are received by said ventricular ring electrode and conducted by said first ventricular conductor;
   an EGM amplifier circuit having first and second inputs, adapted to produce an output signal corresponding to a difference between voltages applied to said first and second inputs;
   switching circuitry, adapted to selectively couple said second atrial conductor to said first input of said EGM amplifier circuit and said second ventricular conductor to said second input of said EGM amplifier circuit, such that said atrial electrical signals are applied to said first EGM amplifier circuit input and said ventricular electrical signals are applied to said second EGM amplifier circuit input.

2. A pacemaker system in accordance with claim 1, further comprising:
a telemetry circuit, coupled to said EGM amplifier output and adapted to transmit said EGM amplifier output signal to an external receiver.

3. A pacemaker system in accordance with claim 1, further comprising an electrically conductive pacemaker canister, wherein said switching circuitry is further adapted to selectively couple said pulse generator to said second atrial conductor and said second ventricular conductor, such that said cardiac stimulating pulses are applied to said heart from said ventricular and atrial tip electrodes, said pacemaker canister adapted to serve as an indifferent electrode.

4. A pacemaker system in accordance with claim 1, wherein said EGM amplifier circuit further comprises filtering circuitry.

5. A method of cardiac pacing and sensing comprising the steps of:

(a) disposing a distal end of an atrial bipolar pacing and sensing lead with atrial tip and ring electrodes in a patient's atrium;
(b) disposing a distal end of a ventricular bipolar pacing and sensing lead with ventricular tip and ring electrodes in a patient's ventricle;
(c) coupling a proximal end of said atrial lead to an implanted pacemaker having a conductive canister;
(d) coupling a proximal end of said ventricular lead to said implanted pacemaker;
(e) applying electrical signals received by said atrial ring electrode to a first input of an EGM amplifier in said pacemaker;
(f) applying electrical signals received by said ventricular ring electrode to a second input of an EGM amplifier in said pacemaker;
(g) delivering atrial stimulating pulses to said atrium from said atrial tip electrode, said conductive pacemaker canister serving as an indifferent pacing electrode;
(h) delivering ventricular stimulating pulses to said ventricle from said ventricular tip electrode, said conductive pacemaker canister serving as an indifferent pacing electrode.

* * * * *